United States Patent [19]

Bannwarth et al.

[11] Patent Number: 5,278,043
[45] Date of Patent: Jan. 11, 1994

[54] RUTHENIUM-LUMAZINE ENERGY TRANSFER SYSTEMS

[75] Inventors: Wilhelm Bannwarth, Rheinfelden-Beuggen, Fed. Rep. of Germany; Francis Müller, Basel, Switzerland

[73] Assignee: Hoffmann-La Roche Inc., Nutley, N.J.

[21] Appl. No.: 643,313

[22] Filed: Jan. 22, 1991

[30] Foreign Application Priority Data

Jan. 25, 1990 [CH] Switzerland ............................ 235/90

[51] Int. Cl.⁵ ...................... C07H 15/12; C12Q 1/68; G01N 33/566; A61K 49/00
[52] U.S. Cl. ..................................... 536/23.1; 435/52; 435/53; 435/91.1; 435/191; 435/6; 435/91.4; 436/501; 436/527; 436/503; 436/504; 436/537; 436/546; 436/172; 436/800; 422/55; 422/56; 536/24.3

[58] Field of Search ................... 546/10; 424/9, 8, 12; 422/55, 56; 435/6, 52, 53, 91, 191–194; 436/501–504; 436/537, 546, 172, 800; 536/27

[56] References Cited

U.S. PATENT DOCUMENTS 4,980,473 12/1990 Barton .................................. 546/10

OTHER PUBLICATIONS

Abelleira et al. (Apr. 1990), vol. 29 (4), pp. 633–639.

*Primary Examiner*—Robert J. Hill, Jr.
*Assistant Examiner*—Gian P. Wang
*Attorney, Agent, or Firm*—George M. Gould; Dennis P. Tramaloni; Patricia S. Rocha

[57] ABSTRACT

Energy-transfer systems which can be used, inter alia, for measuring distances within or between different molecules are described, comprising derivatives of lumazine and ruthenium, in particular derivatives of DNA or RNA sequences.

8 Claims, 9 Drawing Sheets

G : GUANINE

G : GUANINE

SEQUENCE LISTING ( 1 ) GENERAL INFORMATION:

( i i i ) NUMBER OF SEQUENCES: 10

( 2 ) INFORMATION FOR SEQ ID NO:1:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( i v ) ANTI-SENSE: NO ( x i ) SEQUENCE DESCRIPTION: SEQ ID NO:1:

GTTGACAAGA ATCCTCACAA TACC    24

( 2 ) INFORMATION FOR SEQ ID NO:2:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( i v ) ANTI-SENSE: NO ( x i ) SEQUENCE DESCRIPTION: SEQ ID NO:2:

GACAAGAATC CTCACAATAC C    21

( 2 ) INFORMATION FOR SEQ ID NO:3:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (iii) HYPOTHETICAL: NO (iv) ANTI-SENSE: NO (xi) SEQUENCE DESCRIPTION: SEQ ID NO:3:

AAGAATCCTC ACAATACC                                                             18

(2) INFORMATION FOR SEQ ID NO:4:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO:4:

AATCCTCACA ATACC                                                                15

(2) INFORMATION FOR SEQ ID NO:5:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO:5:

TGGGATAGGT GGATTAT                                                              17

(2) INFORMATION FOR SEQ ID NO:6:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO:6:

CTACTGGGAT AGGTGGA                                                              17

(2) INFORMATION FOR SEQ ID NO:7:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO:7:

```
TCAACGTATG TTCACCG                                                        17
```

(2) INFORMATION FOR SEQ ID NO:8:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO:8:

```
ATAATCCACC TATCCCAGTA GGAGAAAT                                            28
```

(2) INFORMATION FOR SEQ ID NO:9:

(i) SEQUENCE CHARACTERISTICS:
        (A) LENGTH: 49 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO:9:

```
ACCCTATCCA CCTAATAAAA ATATTAGGTG GATAGGGTCA TCCTCTTTA                     49
```

(2) INFORMATION FOR SEQ ID NO:10:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO:10:

```
TATTAGGTGG ATAGGGT                                                        17
```

RUTHENIUM-LUMAZINE ENERGY TRANSFER SYSTEMS

BACKGROUND OF THE INVENTION

The detection and the identification of DNA or RNA can be effected by hybridisations with corresponding complementary nucleotide strands. These hybridisations take place with very high specificity and therefore have a high potential for the diagnosis and detection of diseases (Methods Enzymology 68, 373 [1979]).

One technique for carrying out such hybridisation experiments is the so-called Southern Blot method (J. Mol. Biol. 98, 503 [1975]), which, however, is rather complicated and has the further disadvantage that, as a rule, radioactive isotopes, e.g. $^{32}P$, are used in this technique. This is why many efforts have been made on the one hand to simplify the technique of the hybridisation methods, and on the other hand to replace the radioactivity by suitable non-radioactive reporter molecules.

One possibility for both simplifying the hybridisation technique and, at the same time, replacing the radioactivity is provided by fluorescent systems where an energy transfer takes place from a donor to an acceptor. Such energy-transfer systems were predicted by Förster (Ann. Phys. 2, 55 [1948]). At the same time, Förster (supra) produced a relation between the efficiency of energy transfer and the distance between donor and acceptor (so-called Förster equation). If the emission band of the donor overlaps the absorption band of the acceptor, energy can be transferred from the donor to the acceptor, and the efficiency of this energy transfer decreases with the 6th power of the distance between donor and acceptor. In other words, the intensity of energy transfer increases as the distance between donor and acceptor decreases.

Since then, energy-transfer measurements have become a useful tool for measuring distances both within and between various molecules (Stryer, Ann. Rev. Biochem. 47, 819 [1987])). Such measurements of distance via the efficiency of energy transfer between donor and acceptor molecules are suitable for immunoassays and for DNA Hybridisation assays (J. Biol. Chem. 251, 4172 [1976]; Anal. Biochem. 108, 176 [1980]; Clin. Chem. 29, 1582 [1983]; Chemiluminescent and Fluorescent Probes for DNA-Hybridisation Systems [1985]; Kingsburg, D. T. and Falkow S., Eds., 345-356, Academic Press, New York).

SUMMARY OF THE INVENTION

The present invention relates to novel energy-transfer systems which are suitable for measuring distances both within and between various molecules and which consist of two organic compounds, one of which is a chromophore of the lumazine type and the other, with which it interacts, is a ruthenium complex.

DETAILED DESCRIPTION OF THE EMBODIMENTS

Figure 1:
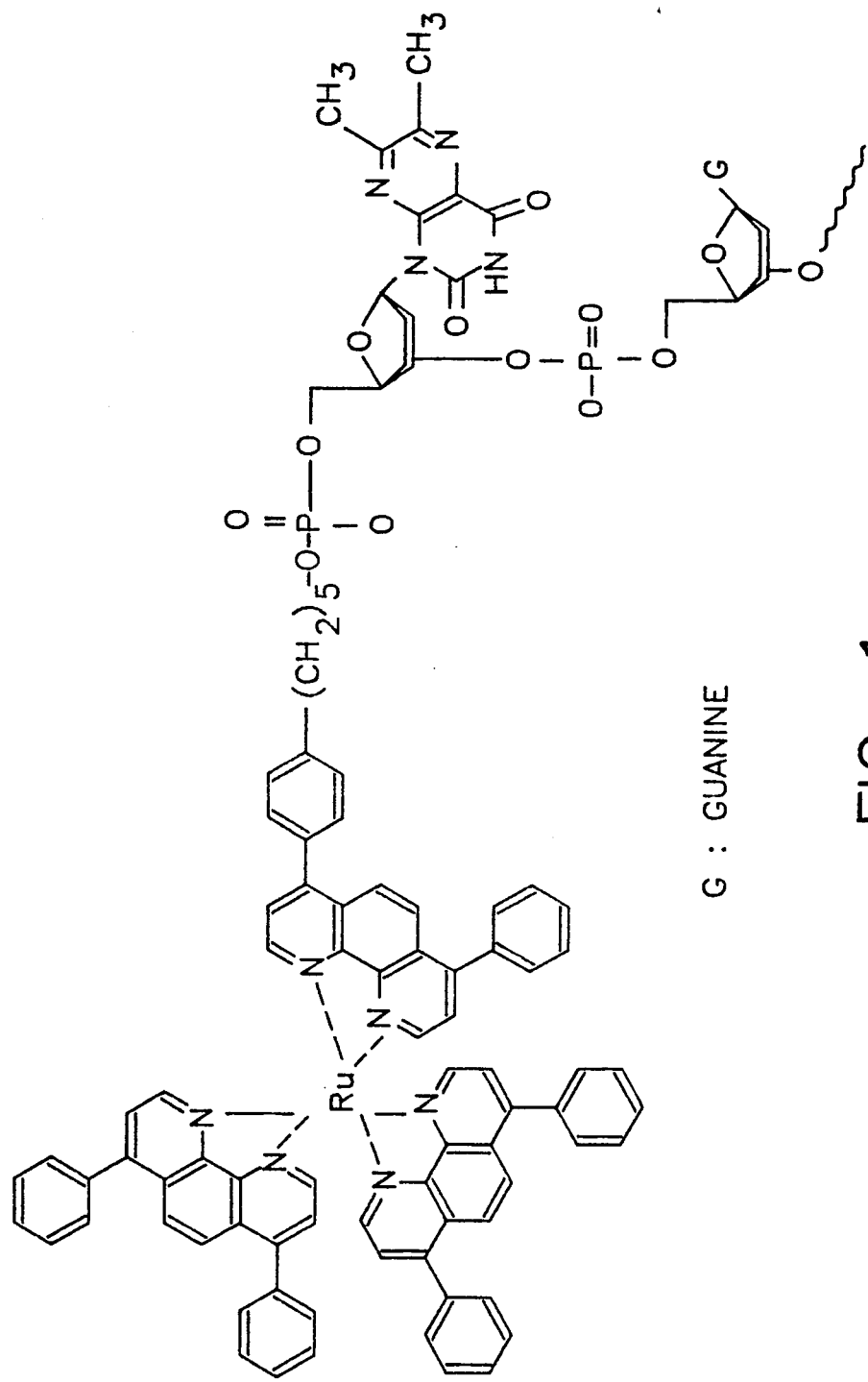
FIG. 1 shows the structure of the 5' end of compound 11 (Example 4).

The present invention relates to novel energy-transfer systems which are suitable for measuring distances both within and between various molecules and which consist of two organic compounds, one of which is a chromophore of the lumazine type and the other, with which it interacts, is a ruthenium complex.

These energy-transfer systems can also, in the wider sense, be defined as donor-acceptor energy-transfer systems. The donor component is to be understood to mean, in general, those compounds which are able to absorb light from an energy source and then release it to an acceptor. By acceptor is generally meant those compounds which are able to absorb this energy released by the donor.

Such acceptors are, according to the present invention, Ru complexes. The energy absorption takes place via the long wavelength metal to ligand charge transfer (MLCT) band of these Ru complexes. The term "metal to ligand charge transfer" (MLCT) band designates the transition from a d electron of the Ru (II) ion to a $\pi^*$ electron of the ligand system of the ruthenium complex. In this connection, see also Crosby, J. Chem. Education 60, 791-796 [1983].

Suitable chromophores of the lumazine type (Lu) are lumazine derivatives and similar $\pi$ systems of the general formula

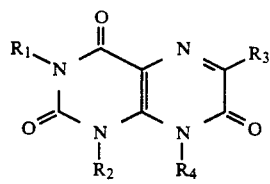

I in which $R_1$ and $R_2$ each represent an H atom, an optionally substituted $C_{1-10}$-alkyl group, 1'-ribosyl, 1'-(2'-deoxyribosyl) or the radical of an analogous hydroxyl compound; $R_3$ represents an H atom or represents an optionally substituted $C_{1-10}$-alkyl group; and $R_4$ represents an optionally substituted $C_{1-10}$-alkyl group; 1'-ribosyl, 1'-(2'-deoxyribosyl) or the radical of an analogous hydroxyl compound, or of the general formula

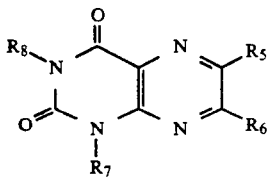

II in which $R_5$ and $R_6$ each represent an optionally substituted $C_{1-10}$-alkyl group; and $R_7$ and $R_8$ represent 1'-ribosyl, 1'-(2'-deoxyribosyl) or the radical of an analogous hydroxyl compound, for example of a C-nucleoside derivative as described in J. Org. Chem. 54, 3927 (1989).

By analogous hydroxyl compounds are meant compounds with one or more hydroxyl groups via which covalent coupling to other molecules can be brought about. By lumazine derivatives are meant both the α and the β anomers. The determination of configuration of the α- and β-anomers is based upon $^1H$-NMR as published in the relevant scientific literature (Chem. Ber. 106, 1401-1417 [1973], Liebigs Ann. Chem. 1217-1234 [1977]). New investigations of ours using X-ray analysis however showed that the formerly designated α-anomere is in reality the β-anomer and vice versa.

The ruthenium complexes are compounds of the general formula

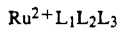

III where the ligands $L_1$, $L_2$ and $L_3$ are identical or different and represent charge-transfer units, and the ligand L3 is substituted by a group A-X where A represents an alkylene group which may be optionally further substituted preferably with sulphonamide, thioether, ether, carboxyl or carboxamide functionalities, and X represents an aldehyde-, carboxyl-, hydroxyl-, amino- or thiocyanate group, halogen or a phosphite or phosphate group or a modified phosphate group, for example a phosphonate or thiophosphate group, or any other suitable functionality, both the optionally substituted alkylene and functional substituent X having as their essential criteria the avoidance of adverse effect on the energy-transfer ability.

As used herein, the term "$C_{1-10}$-alkyl" represents a straight-chain or branched, optionally substituted alkyl chain which contains 1-10 C atoms, such as, for example, methyl, ethyl, n-propyl, isopropyl, n-butyl, isobutyl, sec.butyl, tert.butyl, n-pentyl, n-hexyl, etc. Preferred alkyl groups are methyl groups.

By substituted alkyl groups are meant those which do not have an adverse effect on the energy-transfer ability.

Examples of charge-transfer units $L_1$, $L_2$ and $L_3$ are bipyridyl, bathophenanthroline or benzobathophenanthroline, each of which can optionally be substituted.

The alkylene group A can be straight-chain or branched. A is most preferably a —(CH$_2$)$_4$- or —(CH$_2$)$_5$-group and X is an —OH group.

Preferred energy-transfer systems according to the invention are DNA or RNA sequences which contain covalently bonded chromophores of the lumazine type and which are covalently linked either in modified form, preferably in amino-modified form, or in unmodified form directly or via a spacer group by reaction with a ruthenium complex of the formula III. Covalent bonding at the 5' end of the DNA or RNA sequences, at the 3' end or within the DNA or RNA sequences, which are appropriately modified for this purpose, is preferred.

According to the present invention, the chromophores of the lumazine type can be incorporated at an end of the DNA or RNA sequence or between nucleosides within the DNA or RNA sequence, it being possible for the incorporation to take place in a desired manner. However, it is also possible for several, preferably 2-8, consecutive chromophores of the lumazine type to be incorporated at the end of the DNA or RNA sequence, or within the DNA or RNA sequence. It is also contemplated that appropriately modified chromophores of the lumazine type may be bonded to appropriately modified bases or to the sugar-phosphate backbone.

Particularly preferred energy-transfer systems according to the invention are:

Ru$^{2+}$L$_1$L$_2$L$_3$Lu-SEQ ID No: 1
Ru$^{2+}$L$_1$L$_2$L$_3$GTLu-SEQ ID No: 2,
Ru$^{2+}$L$_1$L$_2$L$_3$GTTGALu-SEQ ID No: 3,
Ru$^{2+}$L$_1$L$_2$L$_3$GTTGACAALu-SEQ ID No: 4 and
Ru$^{2+}$L$_1$L$_2$L$_3$LuLuLuLuLu-SEQ ID No: 1 where the ruthenium complex (Ru complex) of the general formula III is linked via a very stable phosphodiester linkage to the DNA, and the chromophores of the lumazine type are 1-(2'-deoxy-α-D-ribofuranosyl)-6,7-dimethyl-lumazine (Lu) (see FIG. 1).

The chromophores of the lumazine type and ruthenium complexes of the formula III can, however, also be used incorporated in different DNA or RNA sequences as energy-transfer systems. However, they can also be used incorporated in peptides or polypeptides as energy-transfer systems. Equally conceivable is use in other types of molecules.

The term "DNA or RNA sequences" as vised in the specification and claims herein represents natural or synthetically prepared, unmodified or modified DNA or RNA sequences.

The ruthenium complexes of the general formula III can be prepared as described in European Patent Application, Publication No. 178450.

The coupling of the ruthenium complexes of the general formula III to the DNA or RNA sequences which contain one or more chromophores of the lumazine type is carried out in a manner known per se. A possible way of coupling to the modified DNA or RNA comprises treating the ruthenium complex of the formula III and the modified DNA or RNA sequence with a water-soluble carbodiimide derivative, for example with N-cyclohexyl-N'-(2-morpholinoethyl)carbodiimide-methyl-p-toluenesulphonate. A particularly preferred coupling agent is 1,1,3,3-tetramethyl-2-succinyluronium tetrafluoroborate (1:1), called "TSU" hereinafter (the aforementioned "TSU" can be prepared as described in published Japanese Patent application No. 166730/86). The coupling is preferably carried out in a solvent mixture, for example composed of DMF, dioxane or water. It has been found, surprisingly, that activation of carboxyl functionalities with TSU takes places even in the presence of water.

However, the coupling can also be carried out directly, for example via a phosphodiester linkage which is formed in a solvent, such as acetonitrile or absolute pyridine. For a direct coupling, the ruthenium complexes are converted into a form suitable for the coupling, preferably into phosphoramidite, H-phosphonate or activated phosphate functionalities.

The phosphoramidite derivatives of the ruthenium complexes can be prepared in situ for the coupling in the oligonucleotide synthesis (Bannwarth and Schmidt, Tetrahedron Letters 30, 1513 (1989)).

Figure 6:
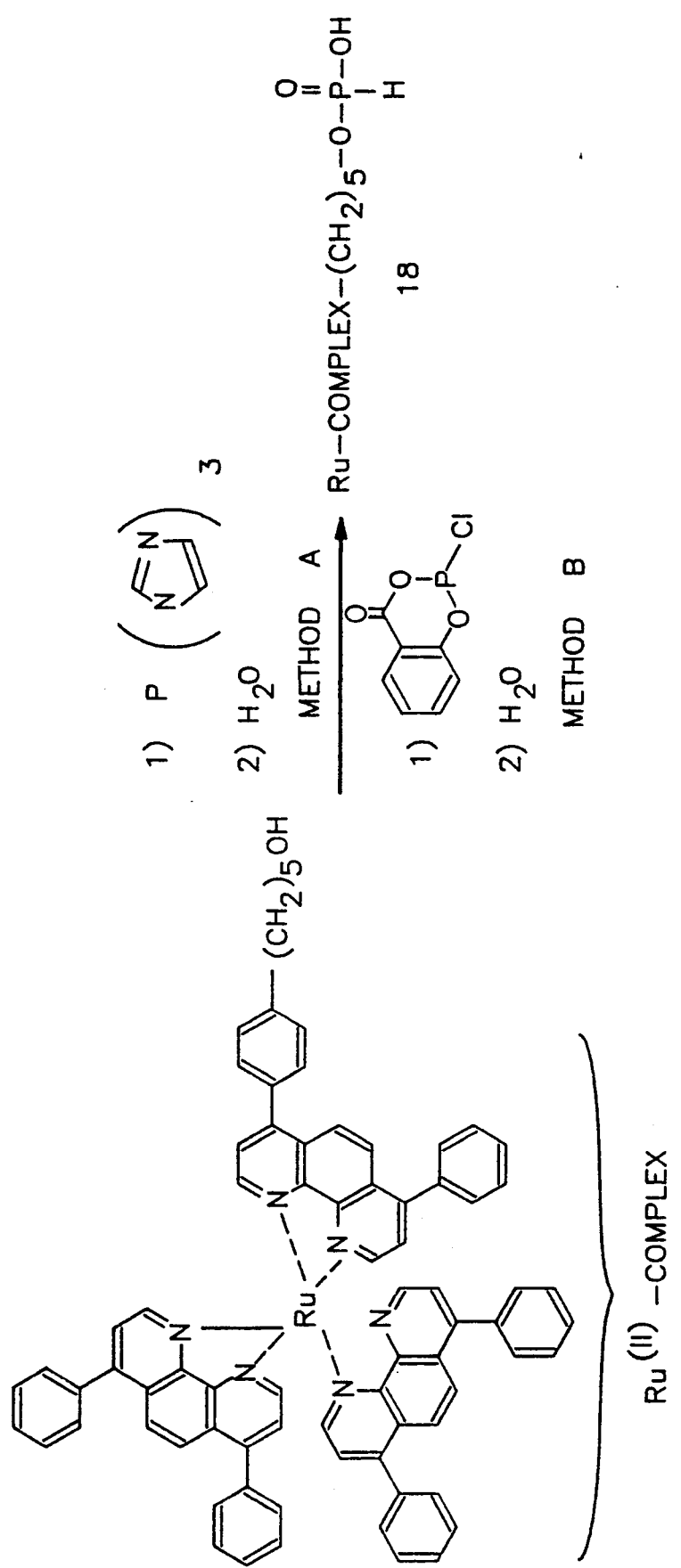
FIG. 6 shows the synthesis of the Ru complex H-phosphonate.

The ruthenium complexes in the form of the H-phosphonates can be obtained by reaction between the ruthenium complex which has been derivatised with a hydroxyalkyl group and trisimidazoylphosphine (Fröhler et al., Nucleic Acid Research 14, 5399 (1986)) or salicylchlorophosphine as reagent (Marugg et al., Tetrahedron Letters, 2271 (1986)) and subsequent hydrolysis. The preparation can be carried out as shown in FIG. 6. The H-phosphonates obtained in this way can be used in a known manner in the synthesis of oligonucleotides (Garreg et al., Chemica Scripta 25, 280 (1985)).

The preparation of the DNA or RNA sequences to which one or more chromophores of the lumazine type are added, is carried out in a manner known per se. The chromophores of the lumazine type are converted into a form suitable for the coupling, preferably into phosphoramidite, H-phosphonate or activated phosphate functionalities. The coupling is preferably carried out on the growing DNA or RNA fragment during the synthesis. The synthesis can be carried out both in liquid phase and on a solid phase, as described, for example, in Science 230, 281 (1985), Chimia 41, 302 or in "Oligonucleotide Synthesis: A practical Approach", IRL Press, Oxford, UK, M. J. Gait, Ed. (1984).

Particularly preferred DNA sequences having one or more chromophores of the lumazine type are:

GTLu-SEQ ID No: 2,
GTTGALu-SEQ ID No: 3,
GTTGACAALu-SEQ ID No: 4,
Lu-SEQ ID No: 1 and
LuLuLuLuLu-SEQ ID No: 1 in which Lu represents 1-(2'-deoxy-α-D-ribofuranosyl)-6,7-dimethyl-lumazine.

The present invention also relates to these DNA or RNA -lumazine derivatives.

The present invention likewise relates to the lumazine derivatives and similar π systems of the general formula

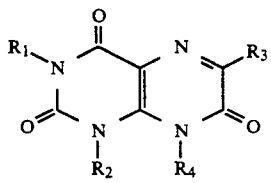

in which $R_1$ and $R_2$ each represent an H atom, an optionally substituted $C_{1-10}$-alkyl group, 1'-ribosyl, 1'-(2'-deoxyribosyl) or the radical of an analogous hydroxyl compound; $R_3$ represents an H atom or represents an optionally substituted $C_{1-10}$-alkyl group; and $R_4$ represents an optionally substituted $C_{1-10}$-alkyl group, 1'-ribosyl, 1'-(2'-deoxyribosyl) or the radical of an analogous hydroxyl compound, or of the general formula

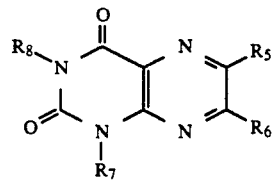

in which $R_5$ and $R_6$ each represent an optionally substituted $C_{1-10}$-alkyl group; and $R_7$ and $R_8$ represent 1'-ribosyl, 1'-(2'-deoxyribosyl) or the radical of an analogous hydroxyl compound, for example of a C-nucleoside derivative as described in J. Org. Chem. 54, 3927 (1989).

In a preferred embodiment, the lumazine derivative has the following formula:

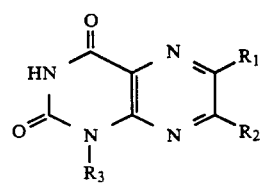

in which $R_1$ and $R_2$ represent an optionally substituted $C_{1-10}$-alkyl group, preferably a methyl group; and $R_3$ represents 1'-ribosyl or 1'-(2'-deoxyribosyl).

Figure 2:
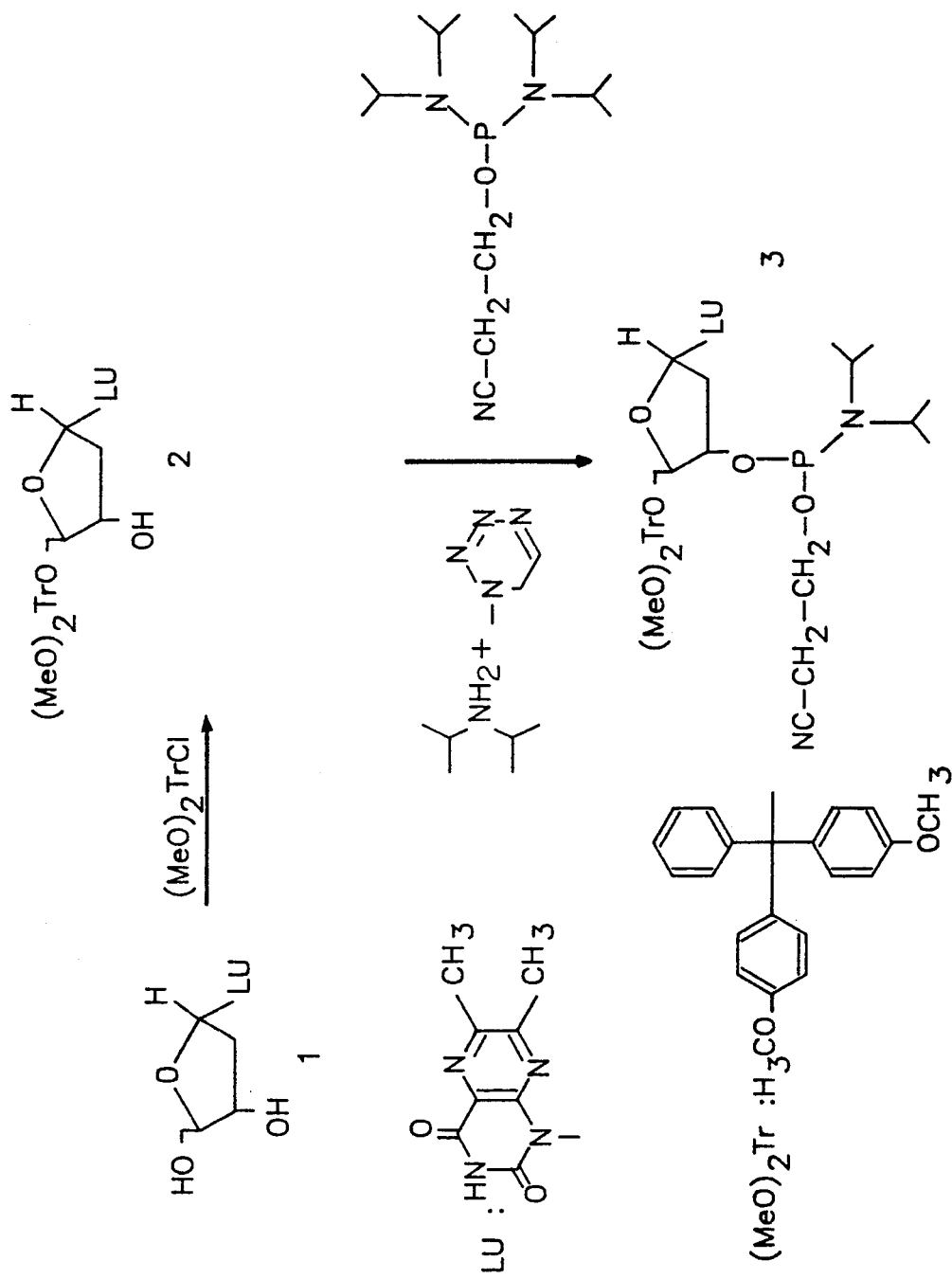
FIG. 2 shows diagrammatically the preparation of 1-(5'-O-4,4'-dimethoxytrityl-2'-deoxy-α-D-ribofuranosyl-3'-O-((2-cyanoethyl)-N,N-diisopropyl-phosphoramidite)-6,7-dimethyl-lumazine 3.

A particularly preferred lumazine derivative is 1-(2'-deoxy-α-D-ribofuranosyl)-6,7-dimethyl-lumazine (see compound 1 in FIG. 2).

The abovementioned lumazine derivatives can be prepared as described by Ritzmann and Pfleiderer in Chem. Ber. 106, 1401 (1973) or in a manner analogous thereto.

The present invention furthermore relates to phosphoramidites and H-phosphonates of the abovementioned lumazine derivatives, which are suitable for the solid-phase or solution syntheses of oligo- or polynucleotides.

A particularly preferred phosphoramidite of the present invention is 1-(5'-O-4,4'-dimethoxytrityl-2'-deoxy-α-D-ribofuranosyl-3'-O-((2-cyanoethyl)-N,N-diisopropylphosphoramidite)-6,7-dimethyl-lumazine (see compound 3 in FIG. 2).

The abovementioned phosphoramidites or H-phosphonates of the lumazine derivatives can be prepared by reacting, by known methods, above-mentioned lumazine derivatives which are protected at the 5' end. It is preferable for the 5' end of the lumazine derivative first to be protected by a 4',4-dimethoxytrityl group, and for the resulting compound then to be reacted with 2-cyanoethoxy-bis-diisopropylaminophosphine in the presence of diisopropylammonium tetrazolide to give the corresponding phosphoramidite of the lumazine derivative. The particularly preferred phosphoramidite, which has already been mentioned herein, 1-(5'-O-4,4'-dimethoxytrityl-2 '-deoxy-α-D-ribofuranosyl-3'-O-((2-cyanoethyl)-N,N-diisopropylphosphoramidite)-6,7-dimethyl-lumazine 3 can be prepared as shown in FIG. 2.

The present invention furthermore relates to lumazine derivatives which allow lumazines to be incorporated at the 3' end of oligonucleotides in solid-phase synthesis.

Figure 5:
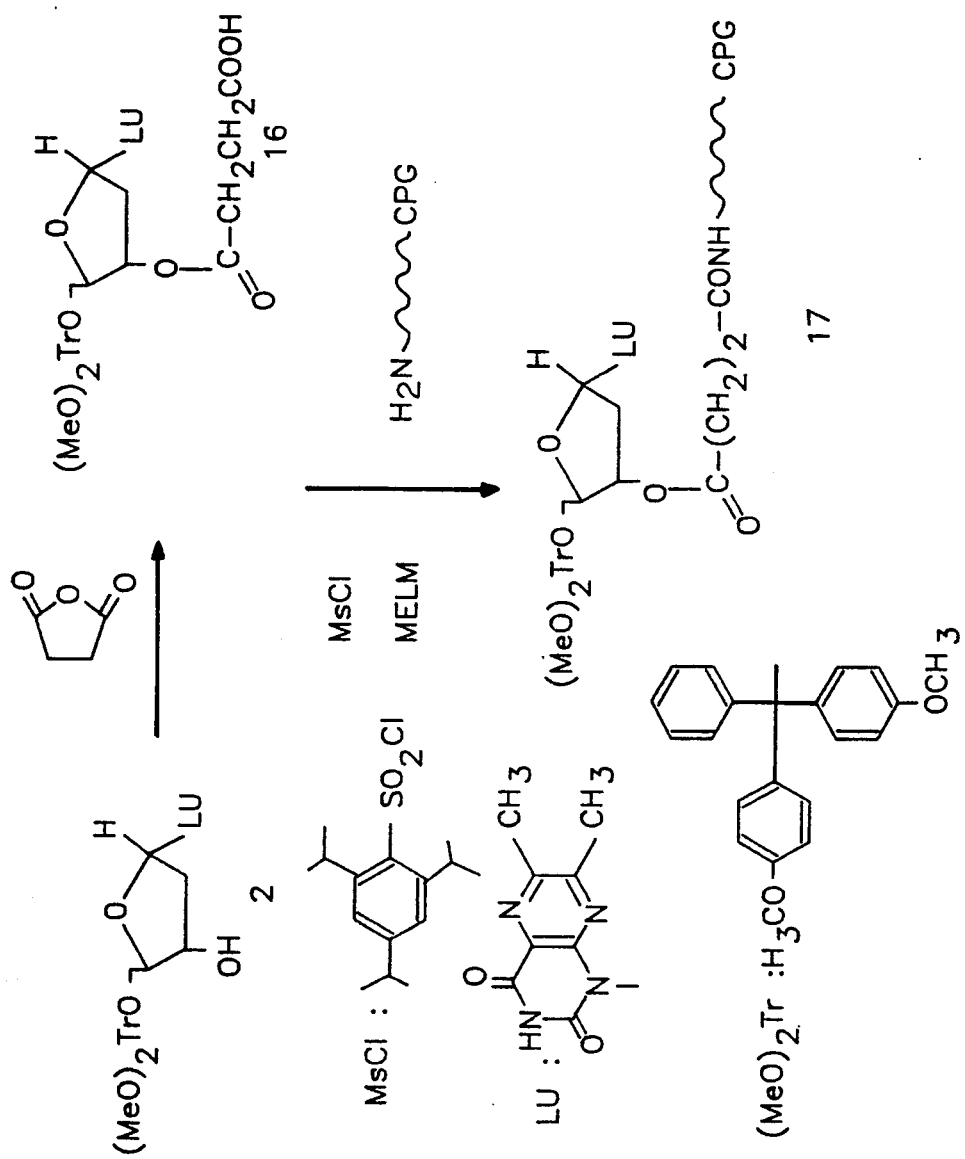
FIG. 5 shows diagrammatically the synthesis of 1-(5'-O-4,4'-dimethoxytrityl-2'-deoxy-α-D-ribofuranosyl-3'-O-succinyl)-6,7-dimethyl-lumazine and of the support modified with lumazine.

A particularly preferred lumazine derivative of the present invention is 1-(5'-O-4,4'-dimethoxytrityl-2'-deoxy-α-D-ribofuranosyl-3'-O-succinyl)-6,7-dimethyl-lumazine (see compound 16 in FIG. 5).

The abovementioned compound can be prepared by reacting, by known methods, the lumazine derivative 2 protected at the 5' end with a 4,4'-dimethoxytrityl group. The protected lumazine derivative is preferably reacted with succinic anhydride with activation, and the product is isolated as salt of the acid. 1-(5'-O-4,4'-dimethoxytrityl-2'-deoxy-α-D-ribofuranosyl-3'-O-succinyl)-6,7-dimethyl-lumazine can be prepared as shown in FIG. 5.

The present invention furthermore relates to controlled pore glass (CPG), which is normally used as support material in solid-phase synthesis, which has been modified with lumazine derivatives (see compound 17 in FIG. 5). Other support materials which can be used for the modification, such as, for example, silica gel, can likewise be utilised (F. Chow; T. Kempe; G. Palm; Nucleic Acids Res. 9, 2807 [1981]).

A wide variety of radicals can be incorporated at the 3'end of an oligonucleotide by the linkage of the CPG material to nucleosides and derivatives thereof. In the preferred embodiment of the present invention, the support material is linked to a lumazine derivative which is suitable for the further synthesis of an oligonucleotide.

The functionally modified CPG is prepared in a manner known per se by coupling the 1-(5'-O-4,4'-dimethoxytrityl-2'-deoxy-α-D-ribofuranosyl-3'-O-succinyl)-6,7-dimethyl-lumazine 16 to CPG material suitable for the linkage. In the preferred embodiment, the functionalised support material is prepared as shown in FIG. 5 by activation of 16 with mesitylene-2-sulphonyl chloride (MsCl) and 1-methyl-imidazole (MeIm).

The support obtained in this way can be used to introduce lumazine derivatives at the 3'end of oligo- or polynucleotides. This has the advantage that, for example, energy-transfer systems are possible between oligonucleotides which are equipped with donor or acceptor at different ends of the oligonucleotides.

Particularly preferred energy-transfer systems according to the invention having these properties are:

SEQ ID No: 5-LuLuLuLu    20

SEQ ID No: 6-LuLuLuLu    23

SEQ ID No: 7-LuLuLuLu    24

Surprisingly, it has emerged that the chromophores of the lumazine type according to the present invention are suitable for transferring light from a nitrogen laser to ruthenium complexes of the formula III.

The combinations of chromophore of the lumazine type/ruthenium complex of the formula III thus represent energy-transfer systems (with the chromophore of the lumazine type as donor and the ruthenium complex of the formula III as acceptor) which are extremely suitable for measurements of distances within one or between different molecules because, as already stated in the introduction, the Förster equation means that there is strict correlation between energy transfer and the distance between donor and acceptor.

Such measurements of distance can be used to determine molecular associations between various molecules, for example between DNA or RNA sequences and proteins/peptides when one type of molecule is equipped with the donor and the other with the acceptor. This can be used to detect interactions of these molecules and for detecting the presence or absence of molecules. These detections are particularly suitable for diagnostic assays, such as, for example, immunoassays, receptor screening assays and DNA probe assays.

A coupling of the Ru complexes of the formula III to proteins/peptides has been described in European Patent Application, Publication No. 178 450. The modification of lumazine 2'-deoxyribosides at the 5' end with an amino functionality can be carried out in analogy to that of thymidine (Helv. Chim. Acta 71, 1517 [1988]). The coupling of chromophores of the lumazine type to proteins/peptides via carboxamide linkages is to be brought about in this way. This means that the energy-transfer system according to the invention between a chromophore of the lumazine type and an Ru complex of the formula III can be used in those assays in which distances between proteins/peptides play a part, such as, for example, in immunoassays.

Receptor screening assays can also be designed on this basis.

The incorporation of the energy-transfer system in the same molecule allows measurements of distance to be carried out within one molecule. The incorporation of the components of the energy-transfer system in different molecules also allows, however, measurements of distance between different molecules to be carried out. Systems of this type represent the preferred energy-transfer systems according to the invention.

In addition, the said donors, especially the lumazine derivatives according to the invention, are suitable for replacing the dye laser in the combination of nitrogen and dye laser used for excitation of the ruthenium complexes.

The methodology of the time-resolved fluorescence technique is described, for example, in German Offenlegungsschrift 2628158 or the above-mentioned European Patent Application No. 85.1113777.9 (Publication No. 178450).

The examples which follow illustrate the present invention without restricting it.

EXAMPLES

All the solvents were of extra high purity. The phosphoramidite of the ruthenium (bathophenanthroline) complex was prepared in situ as described by W. Bannwarth and D. Schmidt (Tetrahedron Lett. 30, 1513, 1989). DNA syntheses were carried out on solid supports (Adams et al., J. Am. Chem. Soc. 105, 661 [1983]) by means of phosphoramidite chemistry using published methods, for example that of Sinha et al., Nucleic Acids Res. 12, 4539 (1984) or Bannwarth, Chimia 41, 302 (1987). Time-resolved fluorescence measurements were carried out in a volume of 100 μl using a published apparatus (European Patent Application, Publication No. 178450). Short column chromatography (CC) was carried out as described by Hunt and Rigby (Chem. Ind., London, 1868 [1967]) with silica gel 60 (0.063–0.040 mm, Merck). 1-(2'-Deoxy-α-D-ribofuranosyl)-6,7-dimethyl-lumazine 1 was prepared as described by Ritzmann and Pfleiderer in Chem. Ber. 106, 1401 (1973).

EXAMPLE 1

1-(5'-O-4,4'-Dimethoxytrityl-2'-deoxy-α-D-ribofuranosyl)-6,7-dimethyl-lumazine 2

0.15 mmol (45 mg) of compound 1 was taken up in abs. pyridine and evaporated twice. It was then again dissolved in abs. pyridine (5 ml), 0.25 mmol (85 mg) of 4,4'-dimethoxytrityl chloride was added, and the mixture was stirred at room temperature (RT). After 1 h, 1 ml of methanol was added and, after a further 15 min, the mixture was poured into saturated $NaHCO_3$ solution and extracted three times with 30 ml of methylene chloride ($CH_2Cl_2$) each time. The combined organic phases were dried over $Na_2SO_4$, filtered to remove desiccant and concentrated. The residue was fractionated on 10 g of silica gel by short column chromatography using 100 ml of $CH_2Cl_2/Et_3N$ (99/1) and 100 ml of $CH_2Cl_2/MeOH/Et_3N$ (97/2/1). The pure product fractions were collected and concentrated. The residue was dissolved in 5 ml of chloroform and precipitated by dropwise addition to 150 ml of n-pentane. The precipitate was collected and dried and provided 65 mg (48.3%) of pure product.

EXAMPLE 2

1-(5'-O-4,4'-Dimethoxytrityl-2'-deoxy-α-D-ribofuranosyl-3'-O-((2-cyanoethyl)-N,N-diisopropyl-phosphoramidite)-6,7-dimethyl-lumazine 0.3 mmol (183 mg) of compound 2 (Example 1) was taken up in 15 ml of MeCN (abs.) and evaporated. The residue was then taken up again in 15 ml of MeCN, 0.6 mmol (180 mg) of 2-cyanoethoxy-bis-diisopropylaminophosphine and 0.3 mmol (51 mg) of diisopropylammonium tetrazolide were added and the mixture was stirred for 2 h. The mixture was then poured into 100 ml of saturated $NaHCO_3$ solution and extracted three times with 30 ml of $CH_2Cl_2$. The combined organic phases were dried over $Na_2SO_4$, filtered to remove desiccant and concentrated. The residue was fractionated on 10 g of silica gel by short column chromatography using 100 ml of $CH_2Cl_2/Et_3N$ (99/1) and 100 ml of $CH_2Cl_2/Et_3N$ (98/2). The pure product fractions provided 170 mg (70%) of pure product.

EXAMPLE 3

Synthesis of SEQ ID No: 1 4,

GTLu-SEQ ID No: 2 7,

GTTGALu-SEQ ID No: 3 6,

GTTGACAALU-SEQ ID No: 4 5,

Lu-SEQ ID No: 1 8 and

LuLuLuLuLu-SEQ ID No: 1 9

Figure 3:
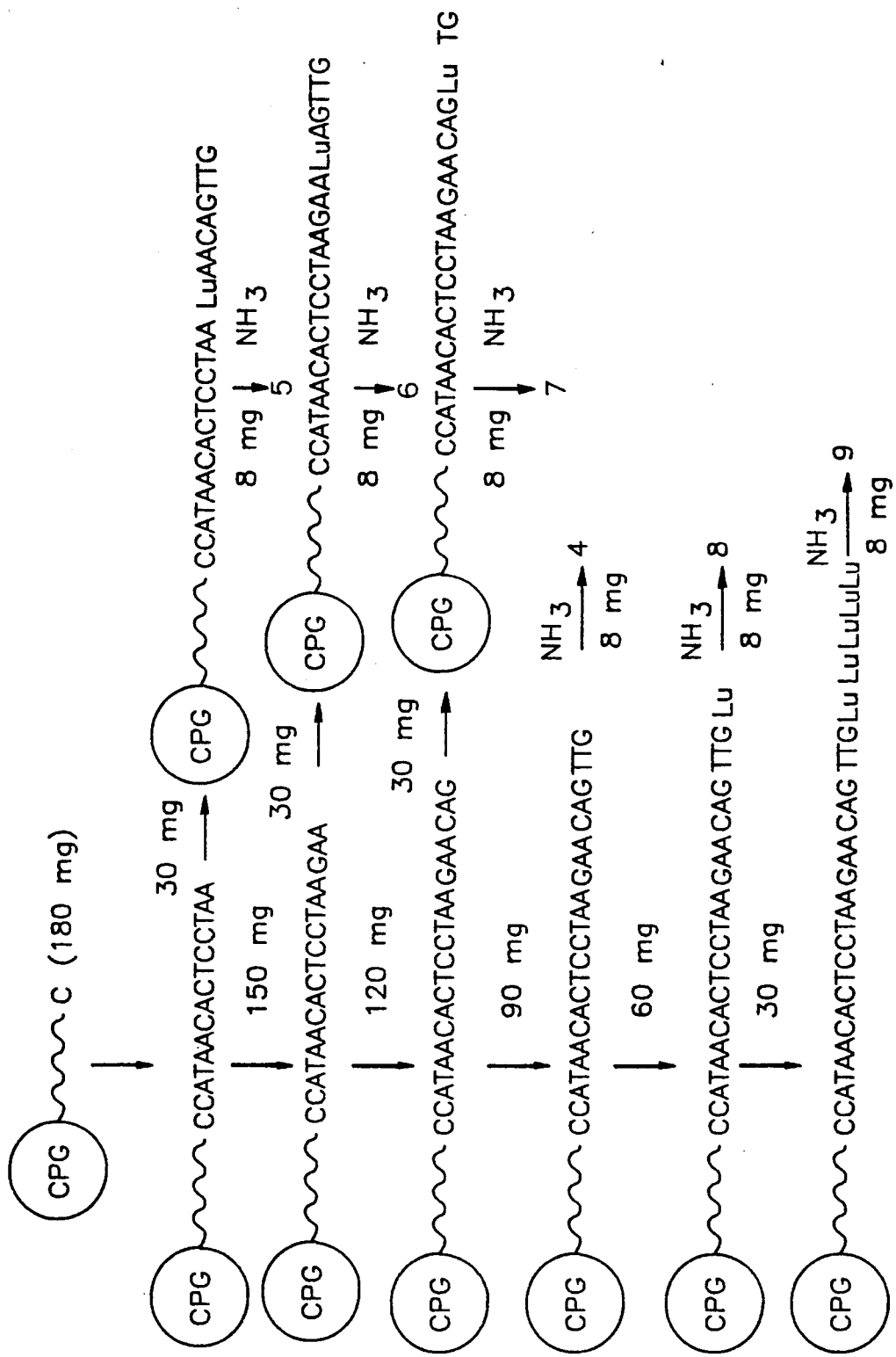
FIG. 3 shows diagrammatically the synthesis of various DNA sequences which have one or more chromophores of the lumazine type incorporated in place of one or more nucleosides or additionally contained at the 5' end of the DNA sequence.
Figure 4A:
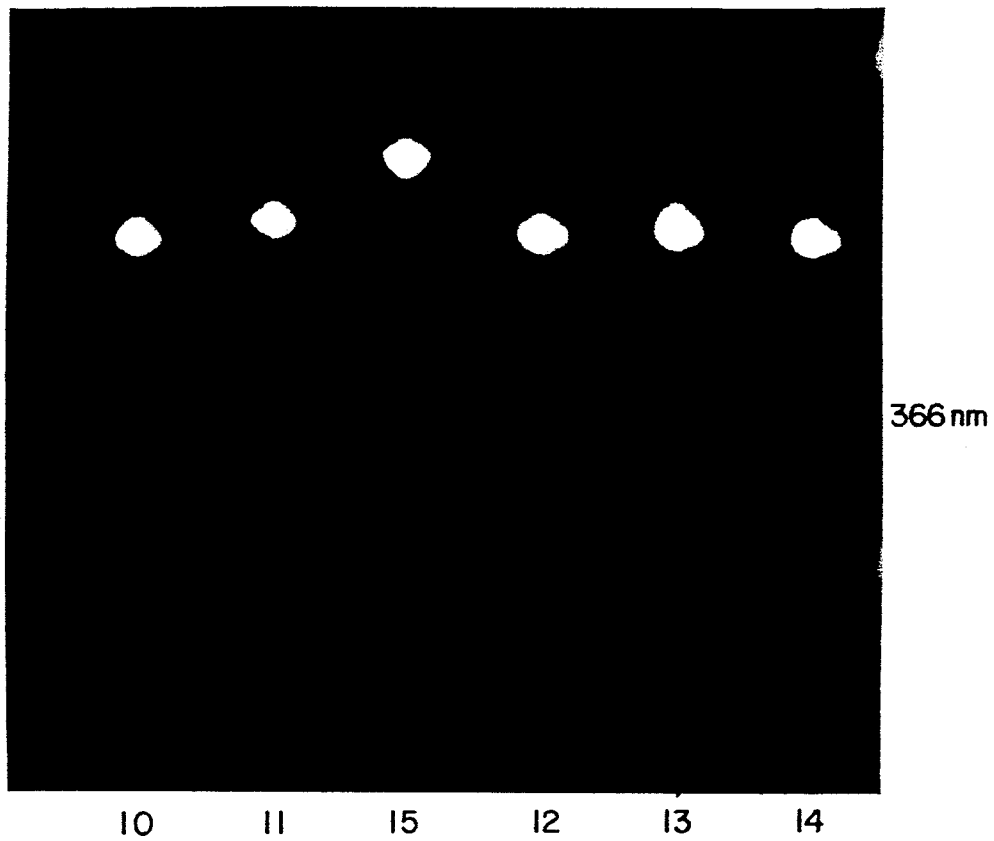
FIG. 4 shows the analysis by gel electrophoresis of compounds 4-9 (Example 3) and 10-15 (Example 4).
Figure 4B:
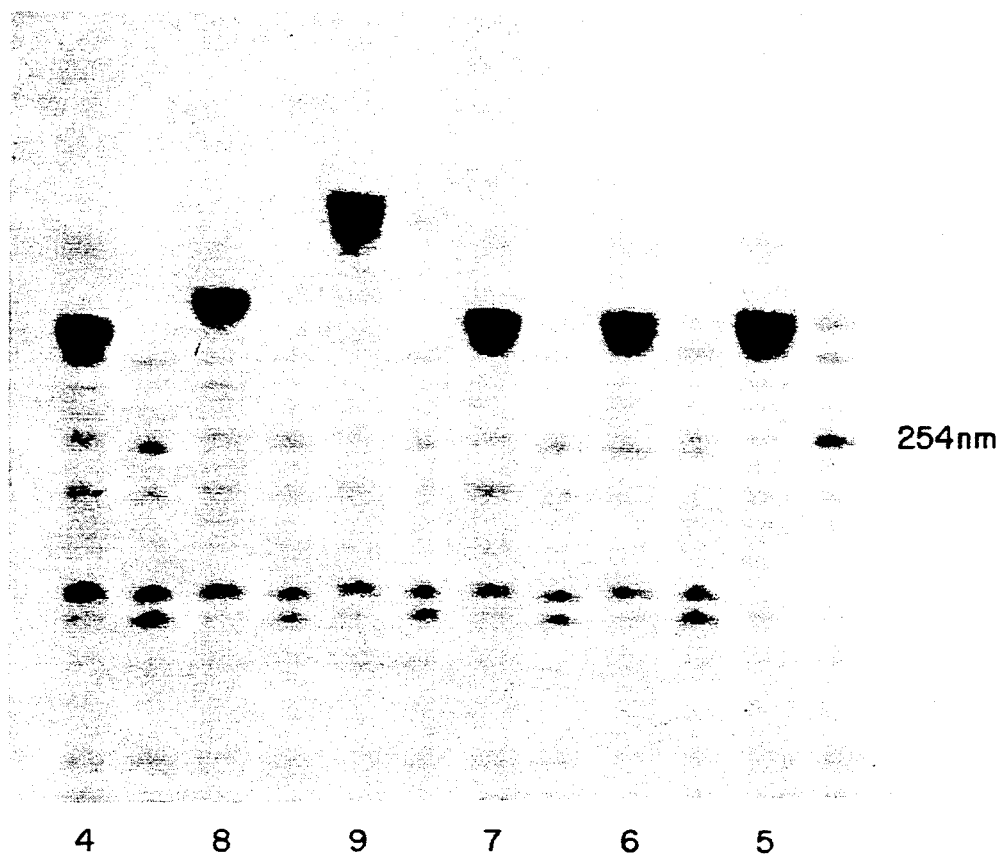

The synthesis was started with controlled pore glass as solid support which was functionalised with 180 mg of C (4.87 μmol) (FIG. 3). The chain extensions were carried out using 40 mg in each case of the appropriate β-cyanoethylphosphoramidite until the lumazine deoxyriboside 3 (Example 2) was incorporated. Each time a lumazine deoxyriboside phosphoramidite 3 was incorporated, 30 mg of solid support material with the corresponding sequence were separated off and the synthesis was continued as shown in FIG. 3. 20 mg of 3 were used for each chain extension with this amidite. 8 mg of each protected sequence still coupled to the solid support material were separated off and, after elimination of protective groups with ammonia, fractionated on a 20% polyacrylamide gel under denaturing conditions (FIG. 4).

EXAMPLE 4

Synthesis of

Ru complex-SEQ ID No: 1 10,

Ru complex-GTLu-SEQ ID No: 2 12,

Ru complex-GTTGALu-SEQ ID No: 3 13,

Ru complex-GTTGACAALu-SEQ ID No: 4 14,

Ru complex-Lu-SEQ ID No: 1 11 and

Ru complex-LuLuLuLuLu SEQ ID No: 1 15

After elimination of the dimethoxytrityl protective group, the bathophenanthroline-ruthenium(II) complex was coupled in the form of its in situ prepared phosphoramidite to the compounds 4–9 (Example 3) (Bannwarth and Schmidt, Tetrahedron Letters 30, 1513 (1989)). The compounds 10–15 were then obtained in impure form by treatment with conc. ammonia. FIG. 4 shows the analysis of these compounds by 20% polyacrylamide gel electrophoresis. Compounds 10–15 were obtained in pure form either by reversed-phase HPLC or by preparative gel electrophoresis and subsequent electroelution.

EXAMPLE 5

Fluorescence measurements with compounds 11–15 to determine the efficiency of energy transfer The fluorescence intensities of compounds 11–15 were measured using the time-resolved fluorescence technique. Compounds 11–15 were excited by pulses of light from a nitrogen laser (0.7 ns at 337 nm), and the fluorescent light was measured using a photomultiplier.

The measured fluorescence intensity $I_F$ at 618 nm (emission wavelength of the ruthenium complex) can be described by the sum of 3 components:

$$I_F = I_{F1} + I_{F2} + I_{F3}.$$

$I_{F1}$ is the lumazine fluorescence intensity at 618 nm. $I_{F2}$ represents the emission of the Ru complex caused by direct excitation, and $I_{F3}$ designates the contribution to the fluorescence intensity from the energy transfer. Since $I_{F1}$ is virtually zero, the measured fluorescence intensity can be written as follows:

$$I_F \sim I_{F2} + I_{F3}.$$

The table which follows lists the efficiencies (E) of energy transfer for compounds 11–15. These were calculated using the formula $$E = \frac{I_F - I_{F2}}{I_{F2}} \cdot 100[\%]$$

| Compound | E (%) |
| --- | --- |
| 11 | 15.0 |
| 12 | 12.6 |
| 13 | 5.4 |
| 14 | 4.1 |
| 15 | 77.0 |

The table reveals a correlation between the efficiency of energy transfer and the distance between donor (chromophore of the lumazine type) and acceptor (ruthenium complex). In addition, the transfer efficiency can be increased by incorporating several donors, as shown by compound 15.

EXAMPLE 6

Synthesis of SEQ ID No: 5-LuLuLuLu 20

A. Synthesis of 1-(5'-O-4,4'-dimethoxytrityl-2'-deoxy-α-D-ribofuranosyl-3'-O-succinyl)-6,7-dimethyl-lumazine 16.

0.29 mmol (175 mg) of compound 2 (Example 1) was taken up in dry pyridine and evaporated several times. The residue was taken up in 5 ml of dry $CH_2Cl_2$, and 0.91 mmol (91 mg) of succinic anhydride, 0.33 mmol (41 mg) of DMAP and 0.91 mmol (126 µl) of $Et_3N$ were added, and the mixture was stirred at room temperature for five hours. The mixture was poured into 10 ml of 1% strength acetic acid and extracted three times with 50 ml of $CH_2Cl_2$ each time. The combined organic phases were dried and concentrated. The residue was purified by column chromatography on 20 g of silica gel using $CH_2Cl_2/Et_3N$ (99/1) and an increasing ethanol gradient (1, 3 and 5%). Pure fractions were collected and concentrated. The product (TLC; Rf: 0.32; $CH_2Cl_2$/MEOH 9/1) was dissolved in 5 ml of $CH_2Cl_2$/1% $NEt_3$ and precipitated in 350 ml of n-pentane. The precipitate was collected and dried. Yield: 165 mg (79%) of 16 as triethylammonium salt.

B. Functionalisation of the CPG Support with 1-(5'-O-4,4'-dimethoxytrityl-2'-deoxy-α-D-ribofuranosyl-3'-O-succinyl)-6,7-dimethyl-lumazine 16 to give compound 17

2.5 g of the CPG support and 0.18 mmol (130 mg) of compound 16 were evaporated in 10 ml of dry pyridine several times. The residue was taken up in 10 ml of dry pyridine, and 4.6 mmol (1.0 g) of mesitylene-2-sulphonyl chloride and 4 mmol (0.4 ml) of 1-methylimidazole were added. The mixture was shaken occasionally during the reaction time (18 hours). The mixture was filtered and washed with pyridine and ether. Unreacted amino groups were blocked by addition of 15 ml of a solution of 1 g of DMAP, 2 ml of $AC_2O$ and 2 ml of lutidine. After 30 minutes the solution was filtered and the functionalised support was washed with pyridine and ether and dried. UV measurement of the eliminated DMTr group (499 nm) revealed that the loading on the support 17 was 27 µmol/g.

C. Synthesis of SEQ ID No: 5-LuLuLuLu 20

The oligonucleotide was synthesized using the support 17 prepared in part B. and using the lumazine phosphoramidite 3 from Example 2. For this, 1.08 µmol (40 mg) of the support were coupled with 24 µmol (20 mg) of the compound 3 and 240 µmol (17 mg) of tetrazole in 0.5 ml of dry MeCN in a standard reaction cycle. After the incorporation of the lumazine chromophores on the 3' end, the synthesis was continued with normal phosphoramidites. After deprotection with $NH_3$, the oligonucleotide 20 was isolated by electroelution after preparative gel electrophoresis.

EXAMPLE 7

Synthesis of Ru complex-SEQ ID No: 8 21

A. Synthesis of the H-phosphonate of the bathophenanthroline-Ru(III) complex 18

Process A:

0.8 mmol (17 µl) of $PCl_3$ was added by syringe to a solution of 2.7 mmol (180 mg) of imidazole and 2.8 mmol (380 µl) of $Et_3N$ in 10 ml of dry MeCN within 5 minutes under argon, and the mixture was stirred at room temperature (RT) for 30 minutes. Separately, 0.1 mmol (126 mg) of the Ru complex was evaporated with dry MeCN and taken up in 10 ml of MeCN and then added to the mixture containing the trisimidazoylphosphine. The mixture was stirred at RT for 2 h and then poured into 100 ml of 0.1 M TEAA pH 7.0 and extracted with $CH_2Cl_2$ ($3 \times 50$ ml). The combined organic phases were dried over $Na_2SO_4$. The residue from evaporation was digested with ether and then washed. 120 mg (86%) of the H-phosphonate 18 were obtained after drying.

Process B:

0.1 mmol (126 mg) of the Ru complex was evaporated with MeCN and dissolved in 5 ml of dry MeCN and 1 ml of dry pyridine, and a solution of 0.5 mmol (101 mg) of salicylchlorophosphine in 2 ml of dry MeCN was added. This reaction mixture was stirred at RT for 1.5 h, poured into 50 ml of 0.1 M TEAA and worked up as described in process A. Yield: 120 mg (86%) of the H-phosphonate 18.

B. Coupling of Ru Complex H-phosphonates to Oligonucleotides

The oligonucleotide with the sequence SEQ ID No: 8 was prepared in a known manner and left on the support with the 5' end deprotected. 26 µmol (36 mg) of compound 18 were evaporated with dry MeCN and dissolved in 1 ml of dry pyridine. 0.5 ml of this solution was added at the same time as 7.3 µl of pivaloyl chloride dissolved in 0.5 ml of dry MeCN to 0.4 µmol of the oligonucleotide SEQ ID No: 8 bound to the support. After a coupling time of 4 minutes, the support was washed and again reacted with the same amount of reagents. This was followed by oxidation with 1 ml of 0.2 M $I_2$/THF and 1 ml of $Et_3N/H_2O$/THF (1:8:1, v/v) and washing steps with MeCN and ether. 10 mg of the support were treated with 700 µl of conc. ammonia at 67° C. for two hours for the deprotection. Polyacrylamide gel electrophoresis showed complete conversion of the initial oligonucleotide into the oligonucleotide 21 labelled with the Ru complex.

EXAMPLE 8

Fluorescence Measurements with Compounds 20–25 to Determine the Efficiency of Energy Transfer In order to determine the energy transfer between lumazine and Ru complex which are each linked to different molecules, the oligonucleotides SEQ ID No: 5-LuLuLuLu 20 and SEQ ID No: 6-LuLuLuLu 23 and the oligonucleotide SEQ ID No: 8 21 labelled with Ru complex were hybridised on a synthetic template SEQ ID No: 9 22 and the energy transfer was determined.

Figure 7:
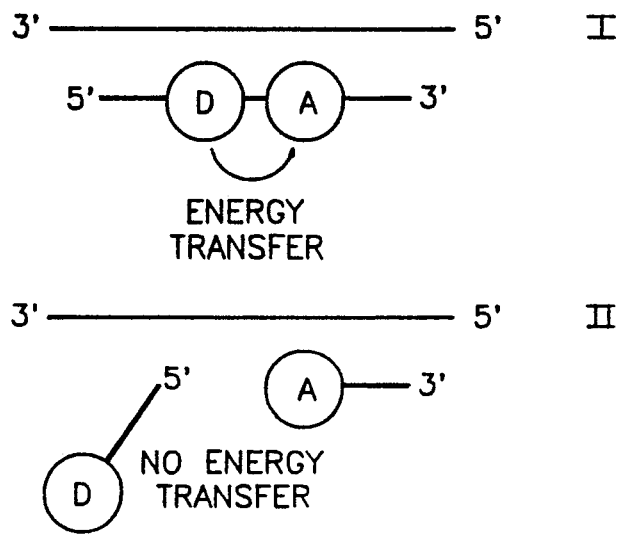
FIG. 7 shows the oligonucleotide sequences 20-25 and their use in energy transfer systems.

The oligonucleotides SEQ ID No: 7-LuLuLuLu 24 and SEQ ID No: 10 25 were employed as negative controls (no energy transfer) (see FIG. 7). To characterise the energy transfer, the following table lists the ratios of the measured fluorescence intensities $I_F$ and $I_{F2}$ of the tested oligonucleotides. The definitions used for $I_F$ and $I_{F2}$ in this connection are those of Example 5.

| Hybrid | $I_F/I_{F2}$ |
|---|---|
| 22/21/25 | 1.0 |
| 22/21/24 | 1.1 |
| 22/21/23 | 1.9 |
| 22/21/20 | 2.2 |

In the cases where oligonucleotides 24 and 25 were used (as negative controls), no energy transfer was observed ($I_F/I_{F2} \sim 1$). Where there was appropriate hybridisation (hybrid 22/21/20 and 22/21/23), energy transfer was possible and was indicated by doubling of the signalling intensity for the fluorescent light from the energy transfer ($I_F/I_{F2} \sim 2$).

Thus measurement of the energy transfer made it possible to state clearly whether hybridisation of the two donor/acceptor oligonucleotides took place on a target which was sought, in this case a DNA sequence.

Figure 8:
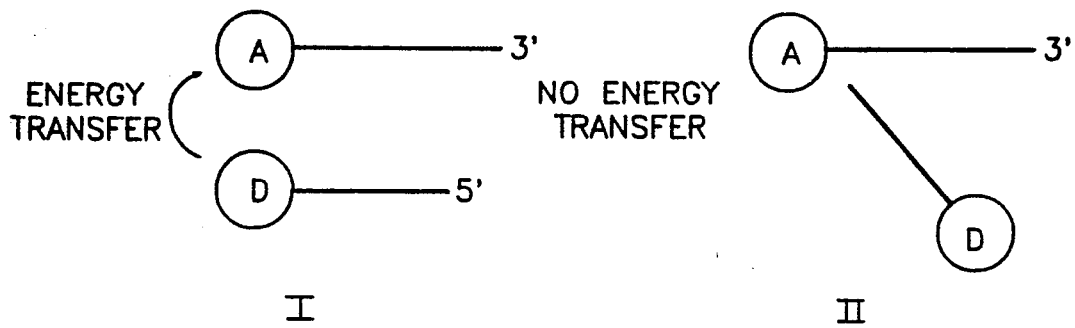
FIG. 8 shows the oligonucleotide sequences 20, 21, 23, 24 and 25 and their use in energy transfer systems.

The same sequences 21-25 were used to determine the energy transfer between two separate molecules without the necessity for the latter, as described above, to be attached by a third molecule (FIG. 8). This made use only of the specificity of recognition between the two compounds of the energy-transfer system. In the present case, the oligonucleotides 21/20 and 21/23 hybridised with one another because of their base composition, and formed with their chromophores an energy-transfer system. By contrast, the oligonucleotide 24 labelled with a chromophore was unable to hybridise with 21. Although the oligonucleotide 25 hybridised with 21 it did not carry a chromophore which was required for an energy-transfer system. As the table below shows, the fluorescence measurements revealed the expected energy transfers only with the pairs 21/20 and 21/23 while the other two pairs 21/24 and 21/25 showed no transfers (controls).

| Hybrid | $I_F/I_{F2}$ |
|---|---|
| 21/20 | 1.9 |
| 21/23 | 1.8 |
| 21/24 | 1.0 |
| 21/25 | 1.0 |

We claim:

1. An energy-transfer system consisting of two organic compounds, one of which is a chromophore of a lumazine type and the other, with which it interacts, is a ruthenium (Ru) complex.

2. The energy-transfer system of claim 1, wherein the chromophore of the lumazine type is a lumazine derivative of the formula

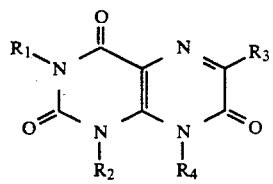

I in which $R_1$ and $R_2$ each represent an H atom, an optionally substituted $C_{1-10}$-alkyl group, 1'-ribosyl, 1'-(2'-deoxyribosyl) or the radical of an analogous hydroxyl compound; $R_3$ represents an H atom or represents an optionally substituted $C_{1-10}$-alkyl group; and $R_4$ represents an optionally substituted $C_{1-10}$-alkyl group; 1'-ribosyl, 1'-(2'-deoxyribosyl) or the radical of an analogous hydroxyl compound, or of the formula

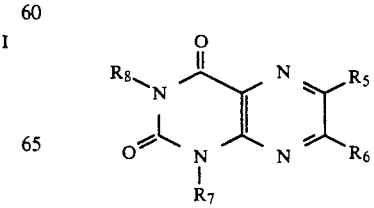

II in which $R_5$ and $R_6$ each represent an optionally substituted $C_{1-10}$-alkyl group; and $R_7$ and $R_8$ represent 1'-ribosyl, 1'-(2'-deoxyribosyl) or the radical of an analogous hydroxyl compound.

3. The energy-transfer system of claim 1 wherein the ruthenium complex is a compound of the formula $$Ru^{2+}L_1L_2L_3 \qquad \qquad III$$

where the ligands $L_1$, $L_2$ and $L_3$ are identical or different and represent charge-transfer units, and the ligand $L_3$ is substituted by a group A-X where A is an optionally substituted alkylene group and X is a functional group which does not adversely affect the energy transfer ability of the complex.

4. The energy-transfer system of claim 3 wherein A represents an alkylene group substituted with sulphonamide, thioether, ether, carboxyl or carboxamide functionalities, and X represents an aldehyde, carboxyl, hydroxyl, amino or thiocyanate group, halogen or a phosphite or phosphate group or a modified phosphate group.

5. The energy-transfer system of claim 2, wherein the chromophore of the lumazine type is a lumazine derivative of formula I in which $R_1$ and $R_2$ each represent an H atom, an optionally substituted $C_{1-10}$-alkyl group, 1'-ribosyl, 1'-(2'-deoxyribosyl) or the radical of an analogous hydroxyl compound; $R_3$ represents an H atom or represents an optionally substituted $C_{1-10}$-alkyl group; and $R_4$ represents an optionally substituted $C_{1-10}$-alkyl group, 1'-ribosyl, 1'-(2'-deoxyribosyl) or the radical of an analogous hydroxyl compound.

6. The energy-transfer system of claim 2, wherein the chromophore of the lumazine type is a lumazine derivative of the formula II in which $R_5$ and $R_6$ represent an optionally substituted $C_{1-10}$-alkyl group; and $R_7$ and $R_8$ represent 1'-ribosyl, 1'-(2'-deoxyribosyl) or the radical of an analogous hydroxyl compound.

7. The energy-transfer system according to any of claims 1-6, characterised in that one or more chromophores of the lumazine type are incorporated at the end of a DNA or RNA sequence or within a DNA or RNA sequence and the ruthenium complex is of the formula III in which the charge-transfer units $L_1$, $L_2$ and $L_3$ are identical or different and represent optionally substituted bipyridyl, bathophenanthroline or benzobathophenanthroline groups, said ruthenium complex being bound to the same or different DNA or RNA sequence as the lumazine.

8. Energy-transfer system of claim 7 of the following formulae $Ru^{2+}L_1L_2L_3$- Lu-SEQ ID No: 1,
$Ru^{2+}L_1L_2L_3$- GTLU-SEQ ID No: 2,
$Ru^{2+}L_1L_2L_3$- GTTGALU-SEQ ID No. 3,
$Ru^{2+}L_1L_2L_3$- GTTGACAALU-SEQ ID No: 4 or
$Ru^{2+}L_1L_2L_3$- LuLuLuLuLu-SEQ ID No: 1 in which the ruthenium complex of the general formula III is linked via a stable phosphodiester linkage to the DNA or RNA, and the chromophores of the lumazine type are 1-(2'-deoxy-α-D-ribofuranosyl)-6,7-dimethyl-lumazine [Lu].

* * * * *